(12) United States Patent
Yu et al.

(10) Patent No.: US 9,399,076 B2
(45) Date of Patent: Jul. 26, 2016

(54) OPTICAL SENSOR FOR IN VIVO DETECTION OF ANALYTE

(75) Inventors: Yihua Yu, Birkerod (DK); Jesper S. Kristensen, Virum (DK)

(73) Assignee: MEDTRONIC MINIMED, INC., Northridge, CA (US)

( * ) Notice: Subject to any disclaimer, the term of this patent is extended or adjusted under 35 U.S.C. 154(b) by 2973 days.

(21) Appl. No.: 11/596,589

(22) PCT Filed: May 17, 2005

(86) PCT No.: PCT/EP2005/005328
§ 371 (c)(1),
(2), (4) Date: Nov. 15, 2006

(87) PCT Pub. No.: WO2005/110207
PCT Pub. Date: Nov. 24, 2005

(65) Prior Publication Data
US 2009/0221891 A1    Sep. 3, 2009

(30) Foreign Application Priority Data

May 19, 2004   (GB) .................................. 0411162.1

(51) Int. Cl.
A61B 5/00       (2006.01)
A61K 49/00      (2006.01)
A61B 5/145      (2006.01)

(52) U.S. Cl.
CPC .......... *A61K 49/0004* (2013.01); *A61B 5/14532* (2013.01)

(58) Field of Classification Search
USPC .......... 600/310, 312, 316, 317, 322, 347, 365
See application file for complete search history.

(56) References Cited

U.S. PATENT DOCUMENTS 1,247,522 A    11/1917   Fisher
4,344,438 A     8/1982   Schultz
(Continued)

FOREIGN PATENT DOCUMENTS

WO    WO 91/09312    6/1991
WO    WO 97/19188    5/1997
(Continued)

OTHER PUBLICATIONS

Wilkins et al, "Glucose monitoring: state of the art and future possibilities", Med. Eng. Phys. (1996) 18:273-288.
(Continued)

*Primary Examiner* — Etsub Berhanu
*Assistant Examiner* — Karen Toth
(74) *Attorney, Agent, or Firm* — Nixon & Vanderhye P.C.

(57) ABSTRACT

A sensor for the in vivo detection of glucose comprises: components of an assay for glucose, a readout of which is a detectable optical signal which can be interrogated transcutaneously by external optical means when the sensor is implanted in vivo; and
a shell of biodegradable material encapsulating the assay components while allowing analyte to contact the assay components, wherein the biodegradable material comprises a co-polymer having hydrophobic and hydrophilic units.
A method of preparing such a sensor preferably comprises coacervation, solvent evaporation and/or extraction, spray drying, spray coating, spray chilling, rotary disk atomisation, fluid bed coating, coextrusion and/or pan coating.
A method of detecting glucose using such a sensor suitably comprises implantation of the sensor into the skin of a mammal, transdermal detection or measurement of glucose using external optical means and degradation of the biodegradable material.

23 Claims, 11 Drawing Sheets

(56) References Cited

U.S. PATENT DOCUMENTS

| | | | | |
|---|---|---|---|---|
| 4,368,253 | A | * | 1/1983 | Green et al. ............... 430/326 |
| 4,675,140 | A | | 6/1987 | Sparks et al. |
| 4,679,562 | A | | 7/1987 | Luksha |
| 4,764,317 | A | | 8/1988 | Anderson et al. |
| 5,194,393 | A | | 3/1993 | Hugl et al. |
| 5,246,636 | A | | 9/1993 | Lew et al. |
| 5,277,872 | A | | 1/1994 | Bankert et al. |
| 5,342,789 | A | | 8/1994 | Chick et al. |
| 5,476,776 | A | | 12/1995 | Wilkins |
| 5,514,379 | A | * | 5/1996 | Weissleder et al. ............ 424/426 |
| 6,002,954 | A | | 12/1999 | Van Antwerp et al. |
| 6,163,714 | A | * | 12/2000 | Stanley et al. ............... 600/316 |
| 6,256,522 | B1 | | 7/2001 | Schultz |
| 6,383,220 | B1 | | 5/2002 | van Blitterswijk et al. |
| 6,485,703 | B1 | * | 11/2002 | Cote et al. .................. 424/9.1 |
| 6,671,527 | B2 | * | 12/2003 | Petersson et al. ............. 600/316 |
| 6,911,131 | B2 | * | 6/2005 | Miyazaki et al. ........ 204/403.14 |
| 6,927,246 | B2 | | 8/2005 | Noronha et al. |
| 7,045,361 | B2 | | 5/2006 | Heiss et al. |
| 7,228,159 | B2 | * | 6/2007 | Petersson et al. ............. 600/316 |
| 7,297,548 | B2 | | 11/2007 | Kawanishi et al. |
| 2001/0008931 | A1 | | 7/2001 | Van Antwerp et al. |
| 2003/0013783 | A1 | | 1/2003 | Kommareddi et al. |
| 2010/0290995 | A1 | * | 11/2010 | Pathak et al. ................. 424/9.1 |

FOREIGN PATENT DOCUMENTS

| WO | 00/02048 A | 1/2000 |
|---|---|---|
| WO | WO 00/02048 | 1/2000 |
| WO | WO 02/30275 | 4/2002 |
| WO | WO 03/006992 | 1/2003 |

OTHER PUBLICATIONS

Meadows et al, "Design, manufacture & characterization . . . ", Anal. Chim. Acta, 280 (1993) 21-30.

Jaremko et al, "Advances Toward the Implantable . . . ", Diabetes Care, vol. 21, No. 3, Mar. 1998, pp. 444-450.

Fogt, "Continuous Ex Vivo and In Vivo Monitoring . . . ", Clin. Chem. 36/8(B), 1573-1580 (1990).

Atanasov et al, "Short-term canine implantation . . . ", Med. Eng. Phys., vol. 18, No. 8, pp. 632-640, 1996.

Russell et al, "A Fluorescence-Based Glucose Biosensor . . . ", Analytical Chemistry, 1999, 71, 3126-3132.

Ballerstadt et al, "Competitive-binding assay method . . . ", Analytica Chemica Acta, 345 (1997), 203-212.

Lakowicz et al, "Optical sensing of glucose using . . . ", Analytica Chimica Acta, 271 (1993), 155-164.

Tyagi t al, "Multicolor molecular beacons . . . ", Nature Biotechnology vol. 16, Jan. 1998, p. 49-53.

Fakirov et al, "Poly(ether/ester)s based on . . . ", Makromol. Chem. 191 (1990) 603-614.

Meadow et al, "Fiber-Optic Biosensors Based on . . . ", Talanta, vol. 35, No. 2, 145-150, 1988.

Jeong et al, "Biodegradable block copolymers . . . ", Nature, vol. 388, Aug. 1997, pp. 860-862.

International Search Report of PCT/EP2005/005328, mailed Sep. 2, 2005.

Jeong et al., "Biodegradable Block Copolymers as Injectable Drug-Delivery Systems", Nature, vol. 388, No. 6645, Aug. 28, 1997, pp. 860-862, XP002068338.

* cited by examiner

OPTICAL SENSOR FOR IN VIVO DETECTION OF ANALYTE

This application is the US national phase of international application PCT/EP2005/005328, filed 17 May 2005, which designated the U.S. and claims priority of GB 0411162.1, filed 19 May 2004, the entire contents of each of which are hereby incorporated by reference.

The present invention relates to a sensor, to a method of preparing the sensor and to a method of using the sensor. The sensor may be used in the measurement or monitoring of glucose in body fluid using optical techniques. The sensor is particularly suitable for use in situations in which glucose levels must be closely monitored by taking glucose measurements repeatedly, for example in diabetes management.

In the management of diabetes, the regular measurement of glucose in the blood is essential in order to ensure correct insulin dosing. Furthermore, it has been demonstrated that in the long term care of the diabetic patient better control of the blood glucose levels can delay, if not prevent, the onset of retinopathy, circulatory problems and other degenerative diseases often associated with diabetes. Thus there is a need for reliable and accurate self-monitoring of blood glucose levels by diabetic patients.

Currently, blood glucose is monitored by diabetic patients with the use of commercially available calorimetric test strips or electrochemical biosensors (e.g. enzyme electrodes), both of which require the regular use of a lancet-type instrument to withdraw a suitable amount of blood each time a measurement is made. On average, the majority of diabetic patients would use such instruments to take a measurement of blood glucose twice a day. However, the US National Institutes of Health has recommended that blood glucose testing should be carried out at least four times a day, a recommendation that has been endorsed by the American Diabetes Association. This increase in the frequency of blood glucose testing imposes a considerable burden on the diabetic patient, both in financial terms and in terms of pain and discomfort, particularly in the long-term diabetic who has to make regular use of a lancet to draw blood from the fingertips. Thus, there is clearly a need for a better long-term glucose monitoring system that does not involve drawing blood from the patient.

There have been a number of proposals for glucose measurement techniques that do not require blood to be withdrawn from the patient. Various attempts have been made to construct devices in which an enzyme electrode biosensor is placed on the end of a needle or catheter which is inserted into a blood vessel (Wilkins, E. and Atanasov, P, Med. Eng. Phys (1996) 18: 273-288). Whilst the sensing device itself is located within a blood vessel, the needle or catheter retains connection to the external environment. In practice, such devices are not suitable for use in human patients first because the insertion of a needle or catheter into a blood vessel poses an infection risk and is also uncomfortable for the patient and hence not suitable for long term continuous use. Secondly, devices of this type have not gained approval for use in patients because it has been suggested that the device itself, on the end of a needle or catheter, may be responsible for the shedding of thromboses into the patient's circulation. This obviously poses a very serious risk to the patient's health.

Mansouri and Schultz (Biotechnology 1984), Meadows and Schultz (Anal. Chim. Acta. (1993) 280: pp 21-30) and U.S. Pat. No. 4,344,438 all describe devices for the in situ monitoring of low molecular weight compounds in the blood by optical means. These devices are designed to be inserted into a blood vessel or placed subcutaneously but require fibre-optic connection to an external light source and an external detector. Again the location of these devices in a blood vessel carries an associated risk of promoting thromboses and in addition, in one embodiment the need to retain a fibre-optic connection to the external environment is impractical for long-term use and carries a risk of infection.

In the search for a less invasive glucose monitoring technique some attention has also been focussed on the use of infra-red spectroscopy directly to measure blood glucose concentration in blood vessels in tissues such as the ear lobe or finger tip which are relatively "light transparent" and have blood vessels sited close to the surface of the skin (Jaremko, J. and Rorstad, O. Diabetes Care 1998 21: 444-450 and Fogt, E. J. Clin. Chem. (1990) 36: 1573-80). This approach is obviously minimally invasive, but has proven to be of little practical value due to the fact that the infra-red spectrum of glucose in blood is so similar to that of the surrounding tissue that in practical terms it is virtually impossible to resolve the two spectra.

It has been observed that the concentration of analytes in subcutaneous fluid correlates with the concentration of said analytes in the blood, and consequently there have been several reports of the use of glucose monitoring devices which are sited in a subcutaneous location. In particular, Atanasov et al. (Med. Eng. Phys. (1996) 18: pp 632-640) describe the use of an implantable glucose sensing device (dimensions 5.0× 7.0×1.5 cm) to monitor glucose in the subcutaneous fluid of a dog. The device consists of an amperometric glucose sensor, a miniature potentiostat, an FM signal transmitter and a power supply and can be interrogated remotely, via an antenna and receiver linked to a computer-based data acquisition system, with no need for a connection to the external environment. However, the large dimensions of this device would obviously make it impractical for use in a human patient.

Ryan J. Russell et al, Analytical Chemistry, Vol. 71, Number 15, 3126-3132 describes an implantable hydrogel based on polyethyleneglycol containing fluorescein isothiocyanate dextran (FITC-dextran) and tetramethylrhodamine isothiocyanate concavalin A chemically conjugated to the hydrogel network for dermal implantation. The implanted hydrogel spheres are to be transdermally interrogated.

R. Ballerstadt et al, Analytica Chemica Acta, 345 (1997), 203-212 discloses an assay system in which two polymer (dextran) molecules are respectively labelled with first and second fluorophores and are bound together by multivalent lectin molecules, producing quenching. Glucose saturates the binding sites of the lectin, causing disassociation of the two polymers, giving an increase in fluorescence.

Joseph R. Lakowicz et al, Analytica Chimica Acta, 271, (1993), 155-164 describes the use of phase modulation fluorimetry. This substitutes a fluorescence lifetime based measurement for the fluorescence intensity based measurements taught in the earlier described art.

Fluorescence lifetime can be measured by a phase and modulation technique by exciting fluorescence using light which is intensity modulated at 1 to 200 MHz and measuring the phase shift and the (de)modulation of the emission relative to the incident light.

In WO91/09312 a subcutaneous method and device is described that employs an affinity assay for glucose that is interrogated remotely by optical means. In WO97/19188 a further example of an implantable assay system for glucose is described which produces an optical signal that can be read remotely. The devices described in WO91/09312 and WO97/19188 will persist in the body for extended periods after the assay chemistry has failed to operate correctly and this is a major disadvantage for chronic applications. Removal of the devices will require a surgical procedure.

WO03/006992 deals with this problem by providing the assay in sensor particles which are sufficiently small to be removed from the implantation site by macrophages once the sensor is spent. WO02/30275 provides an apparatus for injecting sensor particles into an upper layer of the skin from which they will be shed by skin growth.

WO00/02048 deals with the problem by using a biodegradable material to contain the assay reagents. Various biodegradable materials are disclosed. These include the biodegradable block co-polymers of Jeong et al., Nature 388: pp. 860-862 which consist of blocks of poly(ethylene oxide) and poly(L-lactic acid). Other materials disclosed are cross-linked proteins, polysaccharides, polyanhydrides, fatty acid/cholesterol mixtures and erythrocyte ghosts.

The present inventors have determined that for optimum performance the biodegradable material should satisfy certain requirements in addition to being biodegradable:
1. The biodegradable material should allow fast permeation so that the sensor has a short response time. This may be achieved if the biodegradable material has a high permeability towards glucose.
2. The biodegradable material should have molecular weight cut-off properties so that glucose can diffuse through the biodegradable material to contact the assay components, but the assay components cannot diffuse through the biodegradable material to move freely around the body.

These properties are not necessarily provided by the materials disclosed in WO00/02048.

Polymers which exhibit clear molecular weight cut-off properties include derivatised cellulose, regenerated cellulose, poly(methylmethacrylate), poly(ethylene-co-vinyl alcohol), poly(carbonate-co-ether), polyacrylonitrile and polysulfone. These polymers are however non-biodegradable.

Biodegradable polymers are usually hydrophobic materials such as poly(lactic-co-glycolic acid), poly-lactic acid, poly-glycolic acid and poly-caprolactone. These materials do not allow glucose diffusion.

The present inventors have now determined that certain co-polymers having hydrophobic and hydrophilic units fulfil all the requirements set out above.

Accordingly, in a first aspect the present invention provides a sensor for the in vivo detection of glucose, comprising:
 components of an assay for glucose, a readout of which is a detectable optical signal which can be interrogated transcutaneously by external optical means when the sensor is implanted in vivo; and
 a shell of biodegradable material encapsulating the assay components whilst allowing analyte to contact the assay components, wherein the biodegradable material comprises a co-polymer having hydrophobic and hydrophilic units.

It is important that the biodegradable material forms a shell. The shell of co-polymer preferably has a thickness of 1 to 100 µm, more preferably 1 to 50 µm.

Preferably, the co-polymer is a random copolymer. Use of a block co-polymer is not preferred, as such polymers typically do not have suitable molecular weight cut-off properties. However, block co-polymers having blocks within the molecular weight limits set out below are suitable for use in the invention.

Preferably, the co-polymer has a permeability of at least $5.0 \times 10^{-10}$ cm$^2$/s.

The word "permeability" is used to refer to the overall permeability of analyte (glucose) through hydrated co-polymer which can be measured experimentally. The permeability is inversely related to the time taken for analyte to equilibrate between the fluid bathing the sensor and the inside of the sensor where it contacts the assay components. Thus, the higher the permeability, the faster the response time of the sensor. A delay of less than 5 minutes in reaching 95% equilibration is desirable.

Preferably, once implanted in the body the co-polymer degrades over a period of one week to one year, for example 30 days. For a typical polymer thickness of 5 µm this corresponds to a degradation rate of 0.17 µm/day. The rate of degradation depends on the water permeability (swelling) and the molecular weight of the polymer. The higher the swelling (corresponding to a high content of hydrophilic domains), the faster the degradation, and the higher the molecular weight, the slower the degradation.

Preferably, for mobility of glucose, the biodegradable material has a molecular weight cut-off limit of no more than 25000 Da. More preferably, the biodegradable material has a molecular weight cut-off limit of no more than 10000 Da. The assay components are of high molecular weight, for example proteins or polymers, in order to prevent their loss from the sensor by diffusion through the co-polymer. In the preferred embodiment wherein the hydrophilic units of the co-polymer comprise an ester of polyethylene glycol (PEG) and a diacid, the molecular weight cut-off limit is affected by the PEG chain length, the molecular weight of the polymer and the weight fraction of the hydrophilic units. The longer the PEG chains, the higher the molecular weight cut-off limit, the higher the molecular weight of the polymer, the lower the molecular weight cut-off limit, and the lower the weight fraction of the hydrophilic units, the lower the molecular weight cut-off limit.

Preferably, the weight fraction of the hydrophobic units is from 10 to 90% of the co-polymer, more preferably from 10 to 50% of the co-polymer.

Preferably, the molecular weight of each hydrophilic unit is from 200 to 10000 Da, more preferably from 400 to 4000 Da. If the molecular weight of the hydrophilic units is too low, glucose permeability will be low.

Preferably, the hydrophilic units of the co-polymer each comprise an ester of polyethylene glycol and a diacid. As an alternative to polyethylene glycol, a mixed polymer of ethylene glycol and propylene glycol may be used, and/or the polyether backbone may be substituted with hydrophobic and/or hydrophilic groups. As a further alternative to polyethylene glycol, poly-tetrahydrofuran (poly-THF) may be used.

Preferably, the hydrophilic units comprise terephthalic acid and/or succinic acid as diacids. Other suitable diacids are oxalic acid, tartaric acid, phthalic acid, aspartic acid, malonic acid and oligomeric or polymeric diacids, for example poly (dimer acid-sebacic acid). In one preferred embodiment, the diacid is terephthalic acid only. In an alternative preferred embodiment, the molar ratio of terephthalic acid to succinic acid is 1:2 to 2:1, suitably 1:1.

Alternatively, the hydrophilic units of the co-polymer may comprise oligomers. Suitable oligomers are oligomers of hydroxyethylmethacrylate (HEMA), vinylpyrrolidone, vinyl alcohol, carbohydrates, ethylene oxide and/or 2-acrylamido-2-methyl propane sulfonic acid. Where the hydrophilic units comprise HEMA, biodegradable linkages (for example ester linkages such as terephthalate linkages) are provided within the polymer to increase biodegradability.

Preferably, the molecular weight of each hydrophobic unit is from 400 to 5000 Da. If the molecular weight of the hydrophobic units is too high, glucose permeability will be low. If the molecular weight of the hydrophobic units is too low, the polymer will have low physical strength.

Preferably, the hydrophobic units of the co-polymer comprise an ester of butane-1,4-diol and a diacid. As an alternative to butane-1,4-diol, pentane-1,5-diol or hexane-1,6-diol may be used.

Preferably, the hydrophobic units comprise terephthalic acid and/or succinic acid as diacids. In a preferred embodiment, the molar ratio of terephthalic acid to succinic acid is 1:2 to 2:1, suitably 1:1. Alternatively, the hydrophobic units comprise terephthalic acid only as diacid. Other suitable diacids are given above.

Alternatively, the hydrophobic units of the co-polymer can comprise oligomers of methylmethacrylate (MMA), polyurethane and/or amides (for example Nylon-6, oligo-N-tertiary butylacrylamide or oligo-N-isopropylacrylamide). Where the hydrophobic units comprise MMA, biodegradable linkages (for example ester linkages such as terephthalate linkages) are provided within the polymer to increase biodegradability.

Preferred polymers have the general formula aPEG(T/S) bPB(T/S)c where "a" denotes the molecular weight of the PEG chain, "b" the weight fraction of the PEG(T/S) (polyethylene glycol terephthalate/succinylate) in the resulting polymer and "c" the weight fraction of the PB(T/S) (polybutylene terephthalate/succinylate) in the resulting polymer. Examples of such polymers are 600PEGT80PST20, 1000PEGT80PBT20, 2000PEGT80PBT20, 4000PEGT80PBT20, 1000PEGT50PBT50 and 1000PEG(T/S)60PB(T/S)40(T/S 50%). The polymers are biodegradable, have high glucose permeability and have molecular weight cut-off properties at around 25000 Da.

Some of these polymers are disclosed in U.S. Pat. No. 6,383,220 and EP1247522.

The assay components are encapsulated by a shell of the co-polymer. One or more assay component chambers may be present within the shell.

Suitably, the assay components are in aqueous solution within the shell.

Another option is for the assay components to be positioned within a matrix of another material which is encapsulated by a shell of the co-polymer.

A third option is for the assay components to be positioned between a core of another material and an envelope of the co-polymer. Three types of such a sensor are of interest.

First, a core material may be used which dissolves in use. Such core materials include lactose spheres (e.g. FlowLac™ from Meggle), mannitol spheres (e.g. Pearlitol™ from Roquette), sucrose/starch spheres (e.g. Pharm-a-Spheres™ from Werners), PVA and PVP. Depending on the nature of the core material, it may be able to diffuse across the envelope of co-polymer to equilibrate with core material in the surrounding fluid, or may be trapped within the sensor. For example, a mannitol core would dissolve and diffuse across the envelope to give a concentration inside the sensor of several μM of mannitol. The typical time taken for complete dissolution of mannitol is 10 to 15 minutes. PVA and PVP would not be able to diffuse across the envelope.

Second, a core material may be used which swells in use to form a matrix into which the assay components can diffuse. Such core materials include cross-linked PEG with acryl, PEGA polymer and agarose.

Third, a core material may be used which neither dissolves nor swells in use. Such core materials include glass. In this case, the assay components can move within the thin shell of space between the core material and the envelope of co-polymer.

The sensor is suitably in the form of one or more fibres or beads. Discs are also a suitable form for the sensor, although they are not preferred.

The sensor may be introduced within the skin by injection, preferably using a syringe, or by other methods, in particular by any method described in WO00/02048. The sensor is preferably of a size suitable for injection through a narrow gauge needle to minimise the discomfort to the patient. Preferably, the sensor has a maximum dimension of 20 μm to 1 mm. However, a rod-shaped sensor having a larger maximum dimension may be used.

The sensor may be introduced within the thickness of the dermis, or subdermally, or may be introduced to the epidermis, although in the latter case it would be likely to be expelled from the skin by outgrowth of the epidermal layers, possibly before the biodegradable material, if present, has degraded.

Because the sensor is located within the skin, an optical signal generated in the sensor can be detected transcutaneously (i.e. through the higher layer(s) of the skin) thus obviating the need for any direct connection between the sensor and the external environment. Once the sensor is in place in a cutaneous location glucose measurements can be taken as often as is necessary with no adverse effects. This is a particular advantage in relation to the long-term care of diabetic patients because if glucose measurements are taken more frequently, tighter control can be maintained over the level of glucose in the blood and the risk of developing conditions related to poorly regulated blood glucose, such as retinopathy, nephropathy, neuropathy, general micro- and macrovascular damage and poor circulation, will be reduced.

Because the sensor of the invention does not itself contain any of the optical components required to interrogate the readout of the assay (these being provided separately and located outside the body) the sensor can easily be provided in a form which is injectable with minimal discomfort to the patient.

Assays suitable for use in the sensor include reactions such as hydrolysis and oxidation leading to detectable optical change i.e. fluorescence enhancement or quenching which can be observed transcutaneously. A preferred assay for use in the sensor of the invention is a binding assay, the readout of which is a detectable or measurable optical signal which can be interrogated transcutaneously using optical means. The binding assay generating the optical signal should preferably be reversible such that a continuous monitoring of fluctuating levels of glucose can be achieved. This reversibility is a particular advantage of the use of a binding assay format in which the components of the assay are not consumed. Binding assays are also preferred for use in the sensor of the invention for reasons of safety as they cannot generate any unwanted products as might be generated by an enzymatic or electrochemical reaction.

Preferred binding assay configurations for use in the sensor of the invention include a reversible competitive, reagent limited, binding assay, the components of which include a glucose analogue and a glucose binding agent capable of reversibly binding both glucose and the glucose analogue. Glucose and the glucose analogue compete for binding to the same binding site on the glucose binding agent. Such competitive binding assay configurations are well known in the art of clinical diagnostics and are described, by way of example, in The Immunoassay Handbook, ed. David Wild, Macmillan Press 1994. Suitable analyte binding agents for use in the assay would include antibodies or antibody fragments which retain a glucose binding site (e.g. Fab fragments), lectins (e.g. concanavalin A), hormone receptors, drug receptors, aptamers and molecularly-imprinted polymers.

Suitable optical signals which can be used as an assay readout in accordance with the invention include any optical signal which can be generated by a proximity assay, such as those generated by fluorescence resonance energy transfer, fluorescence polarisation, fluorescence quenching, phosphorescence technique, luminescence enhancement, luminescence quenching, diffraction or plasmon resonance.

The most preferred embodiment of the sensor of the invention incorporates a competitive, reagent limited binding assay which generates an optical readout using the technique of fluorescence resonance energy transfer. In this assay format, the glucose analogue is labelled with a first chromophore and the glucose binding agent is labelled with a second chromophore. One of the first and second chromophores acts as a donor chromophore and the other acts as an acceptor chromophore.

The fluorescence emission spectrum of the donor chromophore must overlap with the absorption spectrum of the acceptor chromophore, such that when the donor and acceptor chromophores are brought into close proximity by the binding agent a proportion of the energy which normally would produce fluorescence emitted by the donor chromophore (following irradiation with incident radiation of a wavelength absorbed by the donor chromophore) will be non-radiatively transferred to the adjacent acceptor chromophore, a process known as fluorescence resonance energy transfer. This has the result that a proportion of the fluorescent signal emitted by the donor chromophore is quenched, that the lifetime of the fluorescence is changed, and, in some instances, that the acceptor chromophore emits fluorescence. The acceptor chromophore may, however, be a non-fluorescent dye.

Fluorescence resonance energy transfer will only occur when the donor and acceptor chromophores are brought into close proximity by the binding of glucose analogue to glucose binding agent. Thus, in the presence of glucose, which competes with the glucose analogue for binding to the glucose binding agent, the amount of quenching is reduced (resulting in a measurable increase in the intensity of the fluorescent signal emitted by the donor chromophore or a fall in the intensity of the signal emitted by the acceptor chromophore) as labelled glucose analogue is displaced from binding to the glucose binding agent. The intensity or lifetime of the fluorescent signal emitted from the donor chromophore thus correlates with the concentration of glucose in the subcutaneous fluid bathing the sensor.

An additional advantageous feature of the fluorescence resonance energy transfer assay format arises from the fact that any fluorescent signal emitted by the acceptor chromophore following excitation with a beam of incident radiation at a wavelength within the absorption spectrum of the acceptor chromophore is unaffected by the fluorescence resonance energy transfer process. It is therefore possible to use the intensity of the fluorescent signal emitted by the acceptor chromophore as an internal reference signal, for example in continuous calibration of the sensor or to monitor the extent to which the sensor has degraded and thus indicate the need to implant or inject a fresh sensor. The fall of this signal below an acceptable baseline level would indicate the need to implant or inject a fresh sensor.

Competitive binding assays using the fluorescence resonance energy transfer technique which are capable of being adapted for use in the sensor of the invention are known in the art. U.S. Pat. No. 3,996,345 describes immunoassays employing antibodies and fluorescence resonance energy transfer between a fluorescer-quencher chromophoric pair. Meadows and Schultz (Anal. Chim. Acta (1993 280: pp 21-30) describe a homogeneous assay method for the measurement of glucose based on fluorescence resonance energy transfer between a labelled glucose analogue (FITC labelled dextran) and a labelled glucose binding agent (rhodamine labelled concanavalin A). In all of these configurations the acceptor and donor chromophores/quenchers can be linked to either the binding agent or the glucose analogue.

The various FRET chemistries described in the background art cited in the introduction of this document may be used.

Fluorescence lifetime or fluorescence intensity measurements may be made. As described in Lakowicz et al., fluorescence lifetime may be measured by phase modulation techniques.

An alternative to the fluorescence resonance energy transfer is the fluorescence quenching technique. In this case a compound with fluorescence quenching capability is used instead of the specific acceptor chromophore and the optical signal in a competitive binding assay will increase with increasing glucose. An example of a powerful and non-specific fluorescence quencher is given by Tyagi et al. Nature Biotechnology (1998) 18: p 49.

A suitable glucose analogue is dextran. Suitable glucose binding agents are lectins, for example Concanavalin A.

In fluorescence quenching or fluorescence resonance energy transfer dependent assays, the shell structure of the biodegradable material provides sufficient space for fluorophore and quencher molecules to separate when not bound to one another so that quenching of the fluorophore can cease.

In a second aspect, the present invention relates to a method of preparing a sensor as described herein.

The sensor may be prepared by forming an open hollow shell of co-polymer, filling the shell with assay components and sealing the shell to form a sensor.

Extrusion or moulding methods can be used. PEGT-PBT-like polymers (Arnitel™ (DSM) and Hytrel™ (polytetramethyleneglycol-terephthalate-polyalkane-terephthalate; Dupont)) are extensively used for injection moulding, extrusion and blow moulding (film making).

Chemical methods for the preparation of polymer microcapsules include phase separation (coacervation), solvent evaporation and/or extraction.

The coacervation technique relies upon a decrease in the solubility of the coating polymer on addition of a third non-solvent component to the polymer solution. The non-solvent does not dissolve the polymer. During addition of the third component, two liquid phases are formed: the coacervate which is rich in polymer and the supernatant liquid. If the assay chemistry is in droplets dispersed in the polymer solution, they can be coated by the coacervate, so a water-filled core with a polymer shell is formed. The shell is hardened by evaporation or extraction of the polymer solvent. Important parameters in the coacervation process are the ratio of solvent to the third component, polymer concentration, ratio of polymer to assay chemistry, rate of non-solvent addition, nature of surfactant and surfactant concentration. As an alternative to working with solutions, the assay components can be dispersed as a dry micronized powder.

Experiments on phase separation showed the possibility of preparing PEGT-PBT microcapsules using this method. A suitable polymer solvent is dichloromethane. The third component, used to induce phase separation, may for example be silicone oil, sesame oil or cottonseed oil, with a small amount of surfactant (e.g. Span 85™). The hardening agent is suitably heptane.

In the solvent evaporation technique, the polymer is dissolved in a suitable solvent (for example dichloromethane) and dispersed in an aqueous outer phase which is immiscible with the polymer. The aqueous phase contains one or more stabilizers (for example polyvinyl alcohol) to prevent agglomeration of the particles. The organic solvent is evaporated, to yield the hardened particles. The assay components can be dispersed in the organic solution as micronized powder, or as a solution. In order to obtain microcapsules instead of dense microspheres where the assay components are in solution, the composition of the primary emulsion (water-in-oil) has to be carefully selected. The emulsion consists of the assay components in an aqueous solution and the PEGT-PBT polymer dissolved in an organic solvent.

Suitable solvents with a higher water-miscibility than dichloromethane for use in solvent extraction for PEGT-PBT polymers are ethyl acetate, NMP, DMSO and dimethyl isosorbide. DMF and γ-butyrolactone are also suitable solvents. Combinations of solvents may be used.

Suitable physical methods for the preparation of polymer microcapsules include spray drying, spray coating, spray chilling, rotary disk atomisation, fluid bed coating, coextrusion (for example stationary nozzle coextrusion, centrifugal head coextrusion, or submerged nozzle coextrusion) and pan coating.

The spray drying method for capsules generally uses a double nozzle in which a core material (mixed with the assay components) and the shell material (in solution) are combined. Droplets can be formed by ultrasound or vibration and are subsequently hardened by drying (solvent evaporation) in a hardening bath which may be air. The size of the microcapsules and the thickness of the shell can be tailored by varying the nozzle dimensions, the concentration of the solutions and the hardening solvent. For this method, a suitable core material has to be selected (for example agarose, PVP and PVA) if water cannot be used.

In fluid bed coating, pre-formed microspheres of a core material (either mixed with the assay components or coated with the assay components, for example by a preliminary spray coating or fluid bed coating step) are coated with the shell material in solution. Subsequent evaporation of the solvent results in a thin shell layer. When carrying out fluid bed coating, a top spray fluid bed coater (such as the Combi Coata™ fluid bed system) is preferably used to achieve smooth results, but a bottom spray fluid bed coater may also be used.

In spray coating, pre-formed microspheres of a core material (either mixed with the assay components or coated with the assay components, for example by a preliminary spray coating or fluid bed coating step) are coated by spraying of the shell material in solution. Subsequent evaporation of the solvent results in a thin shell layer.

Suitable coating procedures are for example sending cores through several curtains of coating material (U.S. Pat. No. 5,246,636), collecting particles from spray drying and disk drying (U.S. Pat. No. 4,764,317), coating of liquid droplets (U.S. Pat. No. 4,675,140). US2003/0013783 A1 describes the use of a double nozzle system to make capsules.

In a third aspect, the present invention relates to a method of detecting glucose using a sensor as described herein, comprising implantation of the sensor into the skin of a mammal, transdermal detection or measurement of glucose using external optical means and degradation of the biodegradable material.

The sensor is interrogated transcutaneously using optical means i.e. no physical connection is required between the sensor and the optical means. When the sensor incorporates a competitive, reagent limited, binding assay employing the technique of fluorescent energy transfer, the optical means should supply a first beam of incident radiation at a wavelength within the absorption spectrum of the donor chromophore and preferably a second beam of incident radiation at a wavelength within the adsorption spectrum of the acceptor chromophore. In addition, the optical means should preferably be capable of measuring optical signals generated in the sensor at two different wavelengths; wavelength 1 within the emission spectrum of the donor chromophore (the signal generated in connection with the measurement of glucose and wavelength 2 in the emission spectrum of the acceptor chromophore (which could be the glucose signal or the internal reference or calibration signal).

Optical means suitable for use in remote interrogation of the device of the invention include a simple high-throughput fluorimeter comprising an excitation light source such as, for example, a light-emitting diode (blue, green or red), an excitation light filter (dichroic or dye filter) and a fluorescent light detector (PIN diode configuration). A fluorimeter with these characteristics may exhibit a sensitivity of between picomolar and femtomolar fluorophore concentration.

A suitable fluorimeter set-up is shown in the accompanying FIG. 2 and described in the Examples included herein. The fluorimeter separately measures the following parameters:

At wavelength 1 (donor chromophore)
Excitation light intensity, I(1,0)
Ambient light intensity, I(1,1)
Intensity of combined fluorescent and ambient light, I(1,2)
At wavelength 2 (acceptor chromophore)
Excitation light intensity, I(2,0)
Ambient light intensity, I(2,1)
Intensity of combined fluorescent and ambient light, I(2,2)

Measurements are taken by holding the fluorimeter close to the skin and in alignment with the sensor. When making transcutaneous measurements of the fluorescent signals generated in the sensor it is necessary to take account of the absorption of signal by the skin, the absorptivity of human skin is found by experiment to be lowest in the range from 400 nm to 900 nm. The final output provided is the normalised ratio between the fluorescent intensity from the two fluorophores, defined by the following relation (Equation 1):

$$\text{Final output} = (I(1,2) - I(1,1)) * I(2,0) / (I(2,2) - I(2,1)) * I(1,0) \quad (1)$$

The final output from the optical means (e.g. the fluorimeter) as given by Equation 1 above is converted to analyte concentration preferably by means of a computer using calibration data which can be obtained based on the principles set out below.

A calibration curve can be established empirically by measuring response versus glucose concentration for a physiologically relevant range of glucose concentrations. Preferably, this takes place in vitro as part of the production of the sensor device. The calibration procedure can be simplified considerably by using the mathematical relation between response and glucose concentration in a competitive affinity sensor which is derived as follows:

The response of a competitive affinity sensor is governed by the reactions:

$RC \leftrightarrow R + C$ $RL \leftrightarrow R + L$

Designating the dissociation of the complexes RC and RL, formed by the combination of analyte binding agent (R) with analyte (L) or analyte analogue (C).

The corresponding dissociation equilibrium constants are:

$$K_1 = \frac{C_r C_c}{C_{RC}}$$

and, $$K_2 = \frac{C_r C_L}{C_{RL}}$$

where C designates the number of moles of the species in the sensor divided by the sensor volume. Using this measure of concentration both immobilised species and species in solution are treated alike. The mass balance equations are:

$$T_C = C_C + C_{RC}$$

for total analyte analogue concentration and, $$T_R = C_R + C_{RC} + C_{RL}$$

for total analyte binding agent concentration.
Using the expression above, the relation between response and analyte concentration is derived:

$$\frac{T_C - C_C}{C_C} K_1 = \frac{T_R - (T_C - C_C)}{1 + (C_L/K_2)} \quad (2)$$

By using this relation the amount of data necessary for the calibration can be reduced to two key parameters: total analyte binding agent concentration and total analyte analogue concentration. The calibration curve is thus determined by two points on the curve.

The present invention will be further understood with reference to the following non-limiting examples, together with the accompanying figures in which.

Example 1

Permeability tests were carried out to determine the suitability of various materials for use in the sensor of the invention. The polymers were prepared as described in S. Fakirov and T. Gogeva, Macromol. Chem. 191 (1990) 603-614 with a target of 80 wt % hydrophilic segment and 20 wt % hydrophobic segment.

Figure 1:
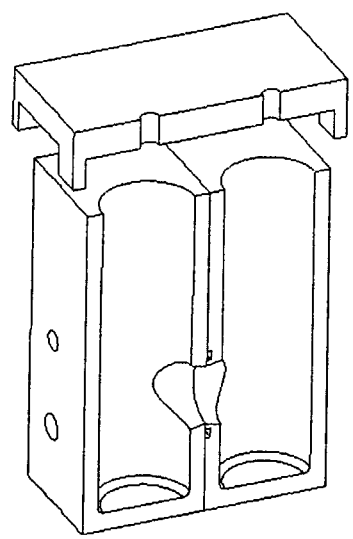
FIG. 1 is a diagram of the permeability cell used in the permeability test of Example 1.

The test was performed in a permeability cell having a donor chamber 10 and an acceptor chamber 12 (FIG. 1). The chambers 10, 12 each had a capacity of 5 mL (or 30 mL in a variant permeability cell). A membrane 14 of the material to be tested was swollen in phosphate buffered saline (PBS) for 30 minutes at room temperature. The membrane was then fixed between the chambers using a rubber O-ring (not shown) to ensure a tight connection between the cell chambers. The membrane was placed on top of one chamber and the second part of the cell was placed very carefully on top of the first part to ensure that membrane was not cut or damaged in any way. The membrane was protected from stirrer bars by the use of a metal mesh inserted into the chamber as any physical contact between the stirrer bars and the membrane would break the membrane.

500 mM glucose (in PBS) was introduced into the donor chamber and PBS introduced into the acceptor chamber. The glucose concentration in the acceptor chamber was measured as a function of time. The measurement was carried out using Glucometer Elite™ test-strips available from Bayer. The test strips were calibrated for use in PBS buffer. Any glucose measuring device could be used but calibration in the media used should be carried out.

Corrected glucose values were used in the calculation of the diffusion coefficient.

Table 1 shows the diffusion results of polymers made as described in Example 1.

TABLE 1

| Membrane description | Thickness (μm) | $D_{glu}$ (cm²/s) | Relative to dialysis memb. | Time for detecting conjugate (days) [1] | Resistance time (day/μm) [2] |
|---|---|---|---|---|---|
| 1000PEGT80PBT20 (Mw ≈ 58 kDa) | 11 | $1.1 \times 10^{-7}$ | 0.22 | >91 | >8.3 |
| 1000PEGT80PBT20 (Mw ≈ 35 kDa) | 26 | $1.6 \times 10^{-7}$ | 0.33 | 36 | 1.4 |
| 2000PEGT80PBT20 | 28 | $3.4 \times 10^{-7}$ | 0.67 | >53 | >1.9 |
| 4000PEGT80PBT20 | 46 | $5.9 \times 10^{-7}$ | 1.18 | >46 | >1.0 |
| 4000PEGT80PBT20 | 25 | $4.4 \times 10^{-7}$ | 0.89 | >46 | >1.8 |

TABLE 1-continued

| Membrane description | Thickness (μm) | $D_{glu}$ (cm²/s) | Relative to dialysis memb. | Time for detecting conjugate (days)[1] | Resistance time (day/μm)[2] |
|---|---|---|---|---|---|
| Dialysis membrane Reg. Cellulose (MwCO 14000) | 16 | $5.0 \times 10^{-7}$ | 1.00 | N/A | N/A |

[1] The number of days it takes to get a certain indication of presence of test conjugate in the acceptor chamber of the diffusion cell.
[2] Resistance time is calculated as the time for detecting the conjugate per unit thickness.

Table 2 shows the collected results of glucose diffusion performed on PEGT-PBT membranes.

TABLE 2

| Membrane Description | Thickness (μm) | ±SD (μm) | Dglu (cm²/s) | Relative to Dialysis memb. |
|---|---|---|---|---|
| 600PEGT80PBT20 | 44 | 7 | $5.0 \times 10^{-8}$ | 0.11 |
| 1000PEGT80PBT20 | 50 | 5 | $1.3 \times 10^{-7}$ | 0.28 |
| 2000PEGT80PBT20 | 78 | 10 | $4.5 \times 10^{-7}$ | 0.98 |
| 1000PEGT80PBT20 | 90 | 5 | $1.8 \times 10^{-7}$ | 0.39 |
| 1000PEGT80PBT20 | 45 | 4 | $1.9 \times 10^{-7}$ | 0.41 |
| Regenerated cellulose MwCO 14 kDa | 60 | 10 | $4.6 \times 10^{-7}$ | 1.00 |

Table 3 shows the results of dextran conjugate diffusion experiments.

TABLE 3

| Membrane Description | Thickness (μm) | ±SD (μm) | Time for detecting conjugate (days)[1] | Resistance time (day/μm)[2] |
|---|---|---|---|---|
| 600PEGT80PBT20 | 44 | 7 | >107 | >2.4 |
| 1000PEGT80PBT20 | 50 | 5 | 90 | 1.8 |
| 2000PEGT80PBT20 | 78 | 10 | 95 | 1.2 |
| 600PEGT80PBT20 | 8 | 3 | >64 | >8.0 |
| 1000PEGT80PBT20 | 8 | 3 | 42 | 5.3 |
| 2000PEGT80PBT20 | 8 | 3 | 41 | 5.1 |
| Regenerated cellulose MwCO 14 kDa | 60 | 10 | >300 | — |

[1] The number of days it takes to get a certain indication of presence of test conjugate in the acceptor chamber of the diffusion cell.
[2] Resistance time is calculated as the time for detecting the conjugate per unit thickness.

A test was carried out for leak of assay chemistry through the membrane. CFSE-Dextran of concentration 2 μM to 10 μM was introduced into the donor chamber and the CFSE-Dextran concentration in the acceptor chamber was measured as a function of time by steady state fluorimetry using a semi-micro cuvette.

Example 2

A glucose assay according to Meadows and Schultz (Talanta, 35, 145-150, 1988) was developed using concanavalin A-rhodamine and dextran-FITC (both from Molecular Probes Inc., Oregan, USA). The principle of the assay is fluorescence resonance energy transfer between the two fluorophores when they are in close proximity; in the presence of glucose the resonance energy transfer is inhibited and the fluorescent signal from FITC (fluorescein) increases. Thus increasing fluorescence correlates with increasing glucose.

The glucose assay was found to respond to glucose, as reported by Schultz, with approximately 50 percent recovery of the fluorescein fluorescence signal at 20 mg/dL glucose. Fluorescence was measured in a Perkin Elmer fluorimeter, adapted for flow-through measurement using a sipping device.

Example 3

Figure 2:
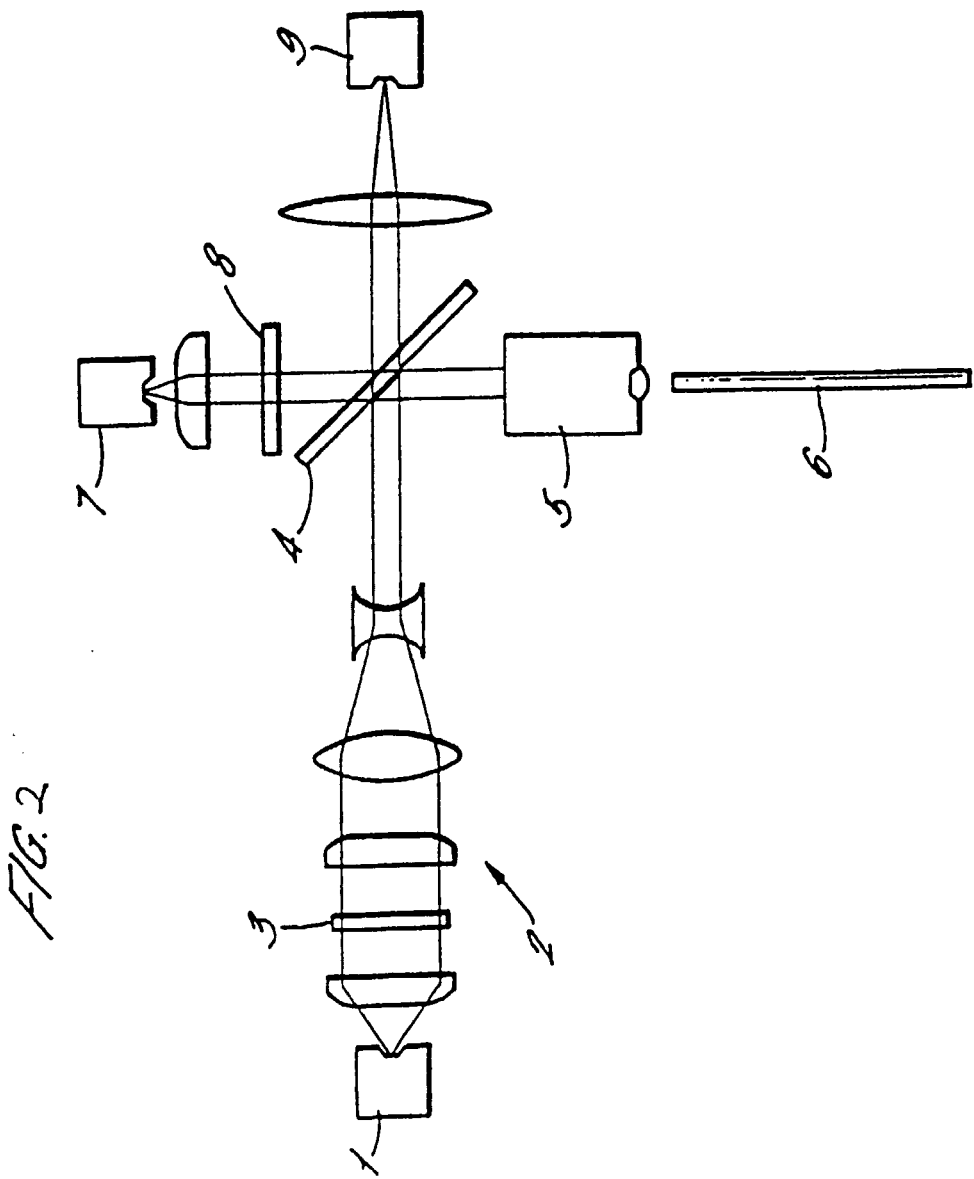
FIG. 2 is a schematic diagram of the optical part of the fibre optic fluorimeter (Example 3)
Figure 3:
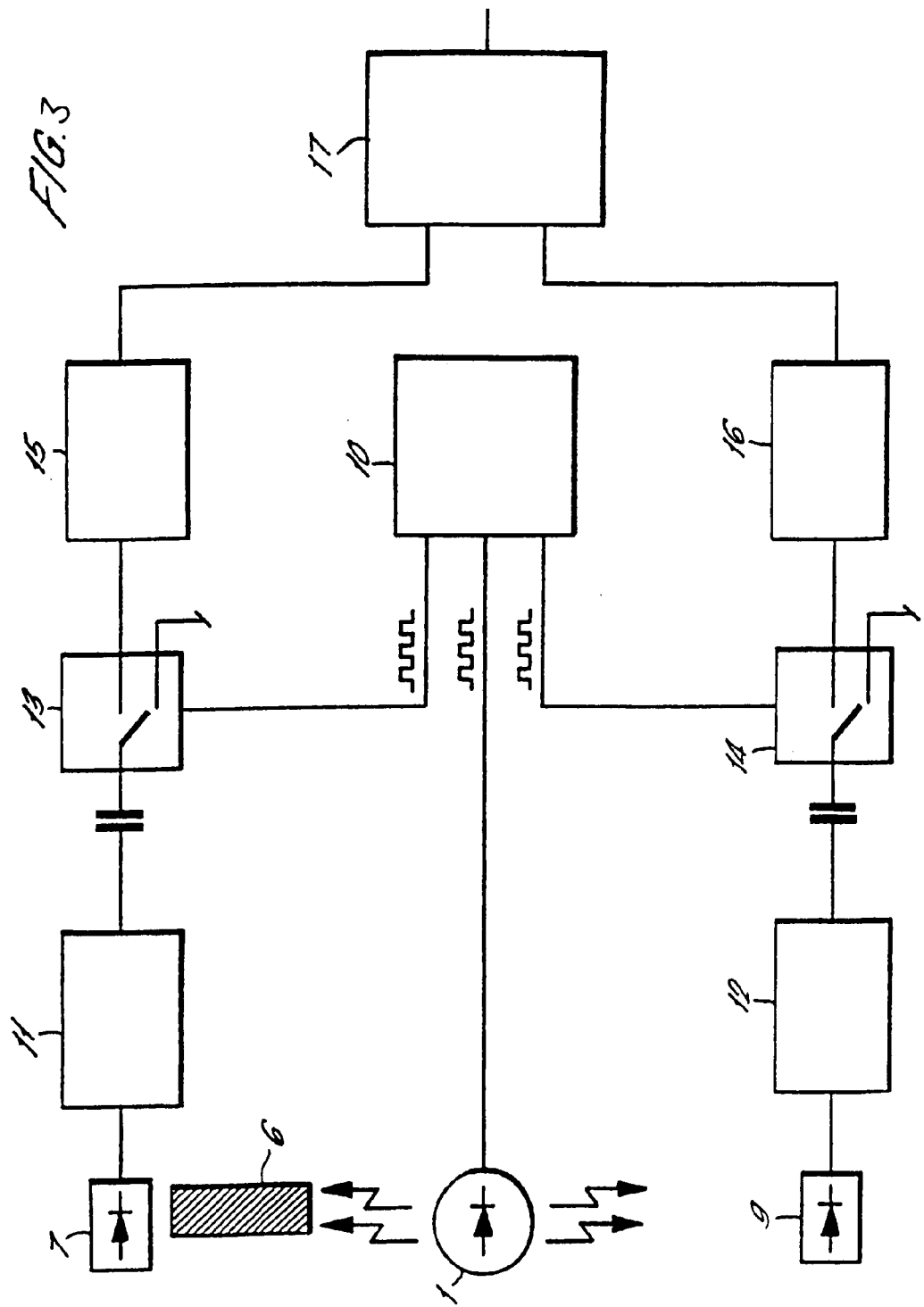
FIG. 3 is a schematic diagram of a driver/amplifier circuit used in conjunction with the optical part of the fibre optic fluorimeter (Example 3)

A fibre optic fluorimeter was assembled as follows.
The optical part of a fibre optic fluorimeter was made from standard components on a micro bench. The set-up, comprising a red LED as light source, lenses, dichroic beamsplitter and filters and detector diodes, was as shown in FIG. 2. Briefly, the fluorimeter comprises a light emitting diode (1) providing an excitation light beam which passes through a condenser (2) containing an excitation filer (3) and is incident upon a beamsplitter (4). Part of the excitatory beam is thereby deflected into launching optics (5) and enters an optical fibre (6). When the fluorimeter is in use in the interrogation of a cutaneously located sensor the end of the skin, in alignment with the cutaneous sensor, so that beam of excitatory light is incident upon the sensor a portion of the optical signal emitted from the sensor following excitation enters the optical fibre (6) and is thereby conveyed into the fluorimeter where it passes through a blocking diode (7). The fluorimeter also contains a reference detector diode (9) which provides a reference measurement of the excitatory light emitted from the LED (1). The ends of a 1 m long Ensign Beckford optical fibre, 0.5 mm in diameter, numerical aperture of 0.65, were ground to a mirror finish using diamond paste on glass paste. One end of the fibre was mounted in an X Y Z holder in front of a 20× microscope objective. The diodes (LED (1) and detector diodes (7) and (9)) were connected to a custom made driver/amplifier circuit as shown in FIG. 3. The circuit comprises a sender (10), current amplifiers (11) and (12), multiplexers (13) and (14), integrators (15) and (16) and analog divider (17). The driver circuit was set to drive the LED (1) at 238 Hz and the signals from the detector diodes (7) and (9) were switched between ground and the storage capacitors (integrator with a time constant of 1 second) synchronised with the drive signal. The two integrated signals correspond to background-corrected fluorescent signal and background corrected excitation light level (LED intensity). The former divided by the latter was supported by an analogue divider as shown in FIG. 3. For test purposes, the distal end of the fibre (6) was dipped into dilute solutions of rhodamine and the optics were adjusted for maximum signal from the analogue divider.

The fluorimeter is battery operated (typical power consumption 150 mA at 9 V) and for convenience can be constructed in the shape and dimensions of a pen.

Example 4

Beads containing assay chemistry were made by a double emulsion solvent evaporation technique in the following manner.

1.0 ml assay chemistry mixture of HMCV1-Dextran 110 kDa (30 µM) and AF594-ConA-succ (30 µM) in PBS was emulsified in 5 ml 10% polymer (1000PEGT80PBT20) solution in dichloromethane together with 1 wt % Span85™ surfactant to form a water-in-oil emulsion. Subsequently, this emulsion was added into 40 ml 10% polyvinylpyrrolidone in a 100 ml flask to form a water-in-oil-in-water emulsion. A vacuum was applied to this emulsion in order to evaporate dichloromethane rapidly. After 5 hours, dark blue microcapsules were collected by filtration and washed several times with PBS buffer (pH 7.4, 50 mM). The obtained beads were stored in a refrigerator (4° C.) prior to the glucose response test.

Example 5

The beads made in Example 4 were washed three times in PBS buffer and left in a front face cuvette to sediment before starting the frequency domain measurements. These measurements were performed in a KOALA (ISS, Champaign Ill., USA). The phase shift between the excitation sin-wave and the emission sin-wave can be converted into fluorescence lifetime but the raw data were used as measured without the need for mathematical treatment). Measurements were made on PBS buffer only and PBS buffer containing 25 mM glucose. When changing the solutions the beads were thoroughly washed with the solution to be measured.

Figure 4:
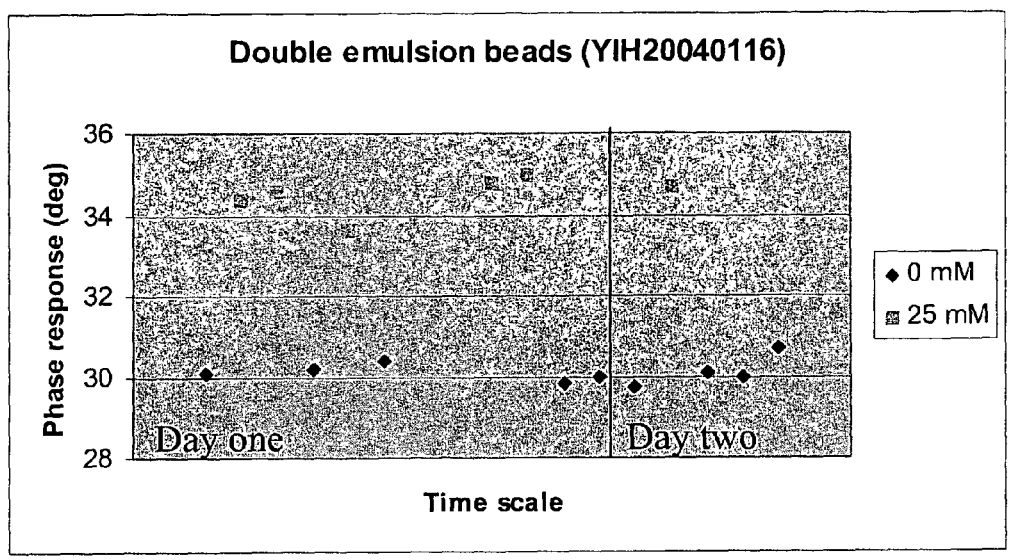
FIG. 4 shows the phase measurements on an assembly of beads tested in Example 5 when exposed to PBS buffer (0 mM glucose) and PBS buffer containing 24 mM glucose over 2 days.

FIG. 4 shows the phase measurements on the assembly of beads when they were exposed to PBS buffer (0 mM glucose) and PBS buffer containing 25 mM glucose. The experiment was run for two days.

Example 6

Figure 5:
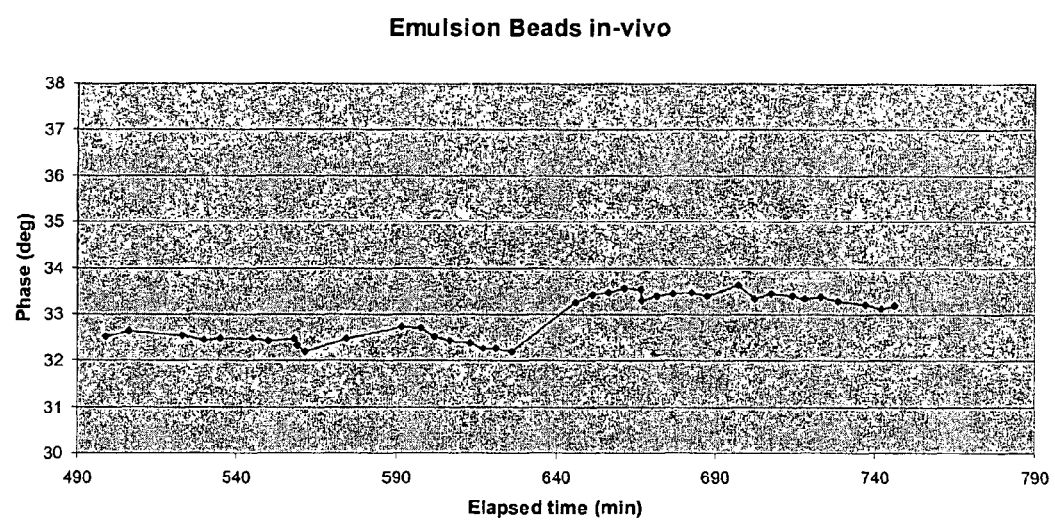
FIG. 5 shows the phase measurements on the interdermally placed beads of Example 6.

The beads made in Example 4 were placed intradermally in the skin of an anaesthetized pig. The phase readout is shown in FIG. 5. The rapid increase in phase after 630 minutes is due to the injection of glucose. The increase corresponds to a rise in glucose of approx 10 mM in the arterial blood.

Example 7

The beads prepared in Example 4 are injected by syringe in the back of the hand of a human volunteer.

A fibre optic fluorimeter (see Example 4) is directed at the skin and a rhodamine fluorescence lifetime signal is obtained and correlated with a conventional blood glucose measurement indicating that transdermal measurements can be made on implanted sensors.

Example 8

Hollow fibres containing assay chemistry were made in the following manner.

Figure 6:
FIG. 6 shows the fibres prepared in Example 8.

The fibres were made by dipping a rod-shaped metal template of diameter 0.4 mm and length 10 cm into a 10% w/v of 1000PEGT80PBT20 polymer solution in chloroform five times with 30 seconds of drying between each submersion. The fibre was removed from the template by swelling the polymer in water. After drying the fibre was cut to the desired length (typical approx. 4 mm) and closed by heat at one end. Assay chemistry prepared from Alexa Fluor™ 594 conjugated Concanavalin A (AF594-ConA) and Hexa-Methoxy Crystal Violet conjugated aminodextran (150 kDa) (HMCV1-dextran) was introduced into the fibre using a thin needle. After filling the other end of the fibre was closed by heat. This yielded a fibre that was similar to that shown in FIG. 6 (2 mm in length).

Figure 7:
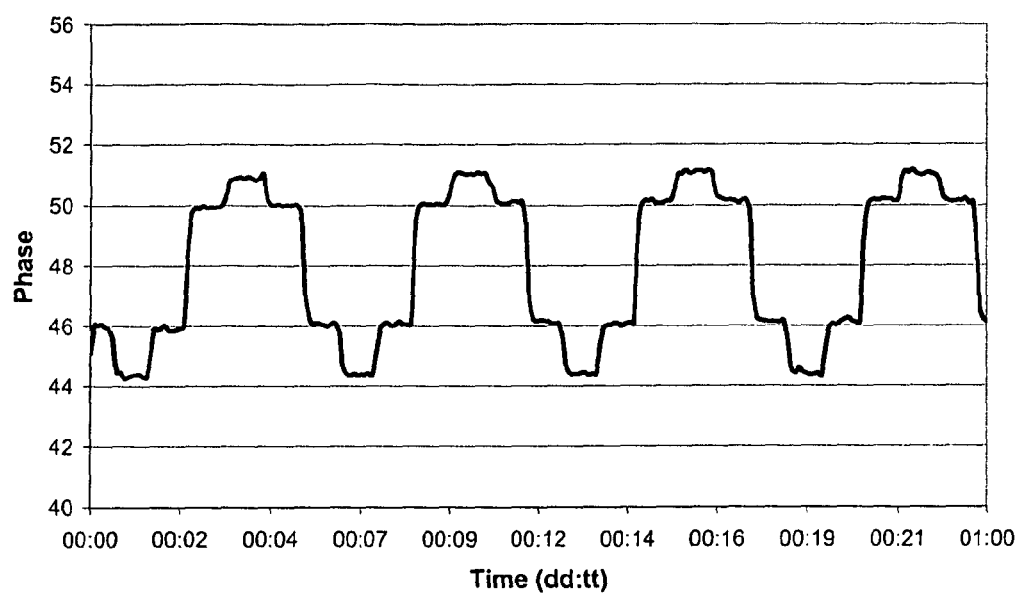
FIG. 7 shows the phase measurements on an assembly of fibres tested in Example 8 containing AF594-ConA and HMCV1-Dextran when exposed to glucose concentrations of 2.5 mM, 5 mM, 25 mM and 50 mM glucose in 10 mM Tris-buffer saline over one day.
Figure 8:
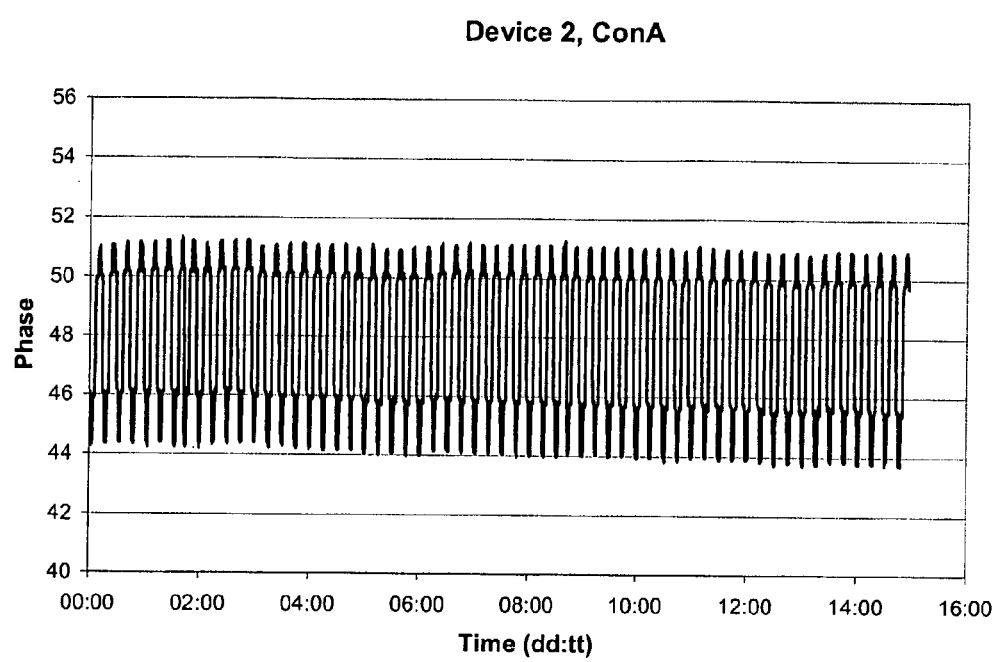
FIG. 8 shows the phase measurements on an assembly of fibres tested in Example 8 containing AF594-ConA and HMCV1-Dextran when exposed to glucose concentrations of 2.5 mM, 5 mM, 25 mM and 50 mM glucose in 10 mM Tris-buffer saline over 15 days.

The fibres were placed in a cuvette containing glucose at a concentration which was varied between 2.5 mM, 5 mM, 25 mM and 50 mM in a Tris-buffer (saline). The fibres were interrogated continuously with a phase fluorometer. FIG. 7 shows the phase measurements for the first day for the experiment and FIG. 8 shows the phase measurements for the complete test of 15 days.

Example 9

Figure 9:
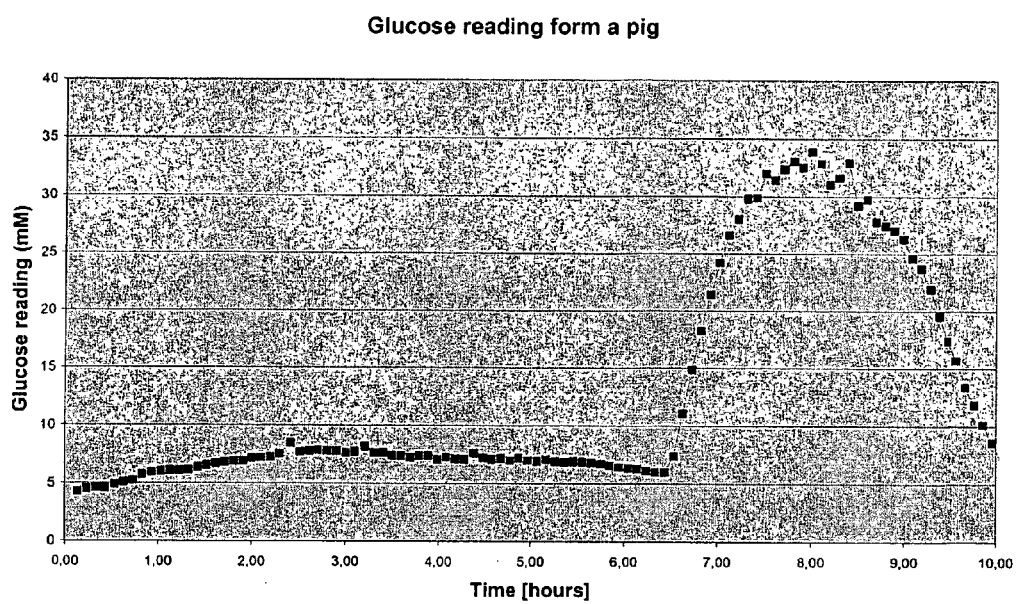
FIG. 9 shows the glucose measurements on the interdermally placed fibres of Example 9.

The fibres made in Example 8 were placed intradermally in the skin of an anaesthetized pig and interrogated with a phase fluorimeter through the skin. The phase readout is shown in FIG. 9. The rapid increase after 6.5 hours is due to the injection of glucose. The increase corresponds to a rise in glucose to 35 mM in the blood.

Example 10

Particles containing mannitol cores loaded with assay chemistry and coated with polymer were made in the following manner.

Figure 10:
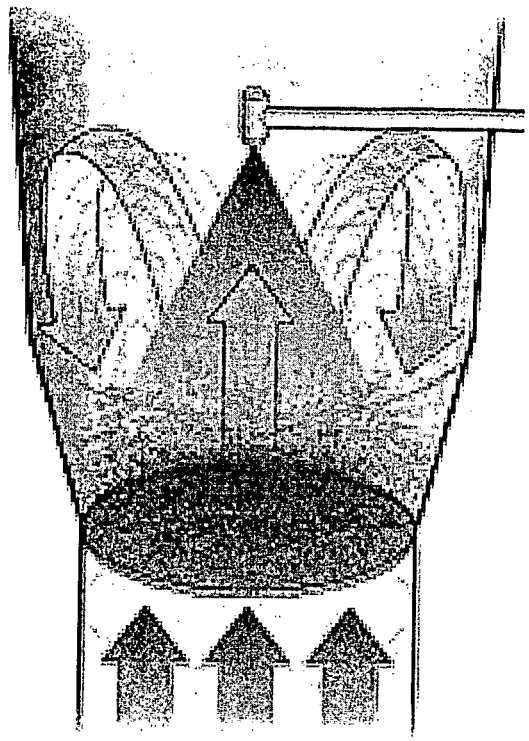
FIG. 10 shows a top spray fluid bed system used in Example 10.
Figure 11:
FIG. 11 shows mannitol cores coated with aqueous fluorescent chemistry and polymer from chloroform solution (Example 10). The twice coated particles are shown in buffer before the entire mannitol core is dissolved.

In a Combi Coata™ top spray fluid bed system (FIG. 10) 50 g of mannitol (e.g. Pearlitol™ 300 SD) spheres sieved to particle size 315 µm to 350 µm were coated with 30 mL aqueous solution of AF594-ConA/HMCV1-Dextran at a temperature of 35° C. The aqueous solution was added to the bed/mannitol spheres at a rate of 1 mL/min.

The temperature in the bed was lowered to 28° C. and the polymer solution (5% w/w 1000PEGT80PBT20 in chloroform) was added at a rate of 1.5 mL/min. In order to get a coating thickness of approx. 20 µm, 20 g of polymer should be added i.e. 400 g of polymer solution which took approx. 3 hours. After drying the particles were immersed in Tris-buffer saline. FIG. 13 shows the swollen shell of polymer and the partially dissolved mannitol core inside the particle. The mannitol core dissolved completely after 10 to 15 minutes.

Example 11

The sensor prepared in Example 10 is injected by syringe in the back of the hand of a human volunteer.

A fibre optic fluorimeter (see Example 3) is directed at the skin and a rhodamine fluorescence lifetime signal is obtained and correlated with a conventional blood glucose measurement indicating that transdermal measurements can be made on implanted sensors.

The invention claimed is:

1. A sensor for the in vivo detection of glucose, comprising:
    components of an assay for glucose, a readout of which is a detectable optical signal which can be interrogated transcutaneously by external optical means when the sensor is implanted in vivo; and
    a shell of biodegradable material encapsulating the assay components whilst allowing an analyte to contact the assay components, wherein the biodegradable material comprises a co-polymer having hydrophobic units and hydrophilic units, the hydrophilic units each comprising an ester of polyethylene glycol and a diacid.

2. A sensor as claimed in claim 1, wherein the co-polymer is a random co-polymer.

3. A sensor as claimed in claim 1, wherein the co-polymer has a molecular weight cut-off limit of no more than 25000 Da.

4. A sensor as claimed in claim 3, wherein the co-polymer has a molecular weight cut-off limit of no more than 10000 Da.

5. A sensor as claimed in claim 1, wherein the co-polymer has a permeability of at least $5.0 \times 10^{-10}$ cm$^2$/s.

6. A sensor as claimed in claim 1, wherein the weight fraction of the hydrophobic units is from 10 to 90% of the co-polymer.

7. A sensor as claimed in claim 1, wherein the hydrophilic units comprise terephthalic acid and/or succinic acid as diacids.

8. A sensor as claimed in claim 7, wherein the hydrophilic units comprise terephthalic acid only as the diacid.

9. A sensor as claimed in claim 7, wherein the ratio of terephthalic acid to succinic acid in the hydrophilic units is between 1:2 and 2:1.

10. A sensor as claimed in claim 7, wherein the hydrophilic units comprise terephthalic acid and succinic acid as diacids.

11. A sensor as claimed in claim 1, wherein the molecular weight of each hydrophilic unit is from 400 to 4000 Da.

12. A sensor as claimed in claim 1, wherein the hydrophobic units of the co-polymer comprise an ester of butane-1,4-diol and a diacid.

13. A sensor as claimed in claim 12, wherein the hydrophobic units comprise terephthalic acid and/or succinic acid as diacids.

14. A sensor as claimed in claim 13, wherein the hydrophobic units comprise terephthalic acid only as the diacid.

15. A sensor as claimed in claim 13, wherein the ratio of terephthalic acid to succinic acid is between 1:2 and 2:1.

16. A sensor as claimed in claim 1, wherein the assay is a binding assay.

17. A sensor as claimed in claim 16, wherein the binding assay is a competitive binding assay, the components of which include a glucose binding agent and a glucose analogue.

18. A sensor as claimed in claim 17 wherein the glucose analogue is labelled with a first chromophore and the glucose binding agent is labelled with a second chromophore, the emission spectrum of the first chromophore or second chromophore overlapping with the absorption spectrum of the second chromophore or first chromophore respectively.

19. A sensor as claimed in claim 17, wherein the binding agent is an antibody, a Fab fragment, a lectin, a hormone receptor, a drug receptor, an aptamer or a molecularly-imprinted polymer.

20. A sensor as claimed in claim 1, wherein the detectable or measurable optical signal is generated by fluorescence resonance energy transfer, fluorescence polarisation, fluorescence quenching, phosphorescence, luminescence enhancement, luminescence quenching, diffraction or plasmon resonance.

21. A method of preparing a sensor as claimed in claim 1, where the method comprises forming the shell of biodegradable material of claim 1 by forming an open hollow shell of co-polymer, filling the shell with assay components and sealing the shell to make the sensor.

22. A method of detecting glucose using a sensor as claimed in claim 1, comprising implanting the sensor into the skin of a mammal, transdermally detecting or measuring glucose using external optical means and degrading the biodegradable material.

23. A method of detecting glucose using a sensor as claimed in claim 1, comprising transdermally detecting or measuring glucose using external optical means by illumination of said sensor present in or below the skin of a mammal.

* * * * *